(12) United States Patent
Inoue

(10) Patent No.: US 9,867,742 B2
(45) Date of Patent: Jan. 16, 2018

(54) DISPOSABLE WEARING ARTICLE

(71) Applicant: UNICHARM CORPORATION, Ehime (JP)

(72) Inventor: Takuya Inoue, Kagawa (JP)

(73) Assignee: Unicharm Corporation, Ehime (JP)

( * ) Notice: Subject to any disclaimer, the term of this patent is extended or adjusted under 35 U.S.C. 154(b) by 737 days.

(21) Appl. No.: 14/372,179

(22) PCT Filed: Feb. 14, 2013

(86) PCT No.: PCT/JP2013/053465
§ 371 (c)(1),
(2) Date: Jul. 14, 2014

(87) PCT Pub. No.: WO2013/132982
PCT Pub. Date: Sep. 12, 2013

(65) Prior Publication Data
US 2015/0202094 A1    Jul. 23, 2015

(30) Foreign Application Priority Data

Mar. 6, 2012 (JP) ................................. 2012-049752

(51) Int. Cl.
*A61F 13/15* (2006.01)
*A61F 13/49* (2006.01)
(Continued)

(52) U.S. Cl.
CPC .... *A61F 13/49012* (2013.01); *A61F 13/4902* (2013.01); *A61F 13/496* (2013.01);
(Continued)

(58) Field of Classification Search
CPC .......... A61F 13/49012; A61F 13/49011; A61F 13/4902; A61F 13/496; A61F 2013/49036; A61F 2013/4948; A61F 13/49413
See application file for complete search history.

(56) References Cited

U.S. PATENT DOCUMENTS

| 4,515,595 | A | * | 5/1985 | Kievit | ............... | A61F 13/49011 |
| | | | | | | 604/385.3 |
| 4,610,678 | A | * | 9/1986 | Weisman | .......... | A61F 13/15203 |
| | | | | | | 604/368 |

(Continued)

FOREIGN PATENT DOCUMENTS

| EP | 2 327 384 A1 | 6/2011 |
| JP | 2001-061890 | 3/2001 |

(Continued)

OTHER PUBLICATIONS

International Search Report from corresponding PCT application No. PCT/JP2013/053465 dated May 14, 2013 (4 pgs).
(Continued)

*Primary Examiner* — Jacqueline Stephens
(74) *Attorney, Agent, or Firm* — Brinks Gilson & Lione

(57) ABSTRACT

A wearing article improved so that an absorbent structure is not apt to be spaced away from the wearer's skin but stuffiness in the wearing article and/or eruption of the wearer's skin can be reliably prevented, which wearing article is a diaper that includes a front waist panel, a rear waist panel and a crotch panel. In the front and rear waist panels, elastics are respectively attached to front and rear waist sheets. The crotch panel includes an absorbent structure containing liquid-absorbent core material and, outboard of the absorbent structure as viewed in a longitudinal direction, front and rear end flaps are formed respectively. The crotch panel includes a first region which includes a
(Continued)

front end of the absorbent structure and the front end flap and overlaps with the front waist panel and a second region which includes a front end of the absorbent structure and the rear end flap and overlaps with the rear waist panel. The first and second regions extend in the longitudinal direction and are joined to respective skin-facing surfaces of the front and rear waist panels by means of first and second joining zones each including a plurality of sub-zones spaced apart from one another in a transverse direction.

20 Claims, 9 Drawing Sheets

(51) Int. Cl.
 *A61F 13/496* (2006.01)
 *A61F 13/494* (2006.01)
(52) U.S. Cl.
 CPC .. *A61F 13/49011* (2013.01); *A61F 13/49413* (2013.01); *A61F 2013/49036* (2013.01); *A61F 2013/4948* (2013.01)

(56) References Cited

U.S. PATENT DOCUMENTS

| | | | |
|---|---|---|---|
| 2004/0158217 A1* | 8/2004 | Wu | ............................. B05C 3/12 |
| | | | 604/385.01 |
| 2007/0239128 A1 | 10/2007 | Takada et al. | |
| 2010/0286646 A1 | 11/2010 | Takino et al. | |
| 2012/0226254 A1 | 9/2012 | Takino | |

FOREIGN PATENT DOCUMENTS

| | | |
|---|---|---|
| JP | 2007-275298 A | 10/2007 |
| JP | 2008-136651 | 6/2008 |
| JP | 2009-061127 | 3/2009 |
| JP | 2009-207565 | 9/2009 |
| JP | 2011-115229 | 6/2011 |
| JP | 2011-115484 | 6/2011 |
| WO | WO 97/48359 | 12/1997 |
| WO | WO 2011/081027 A1 | 7/2011 |

OTHER PUBLICATIONS

European supplementary Search Report from corresponding European application No. 13757631.0 dated Sep. 11, 2015 (8 pgs).

* cited by examiner

FIG.8
(a)
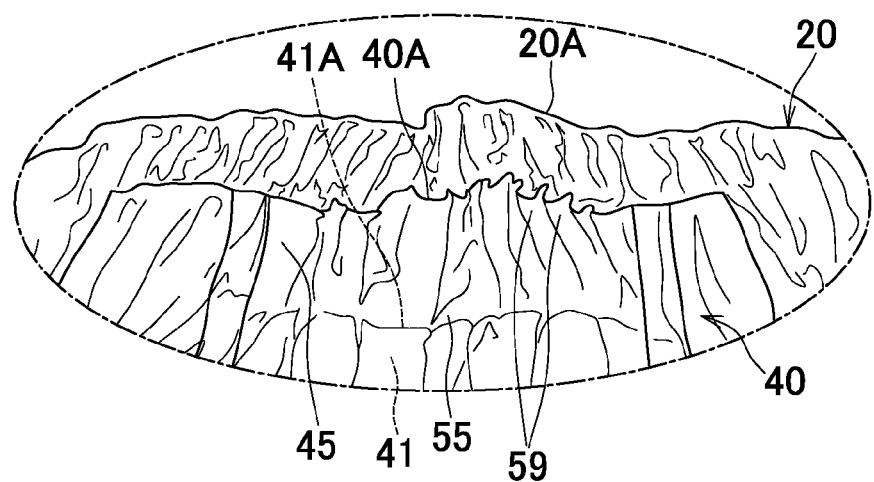
(b)
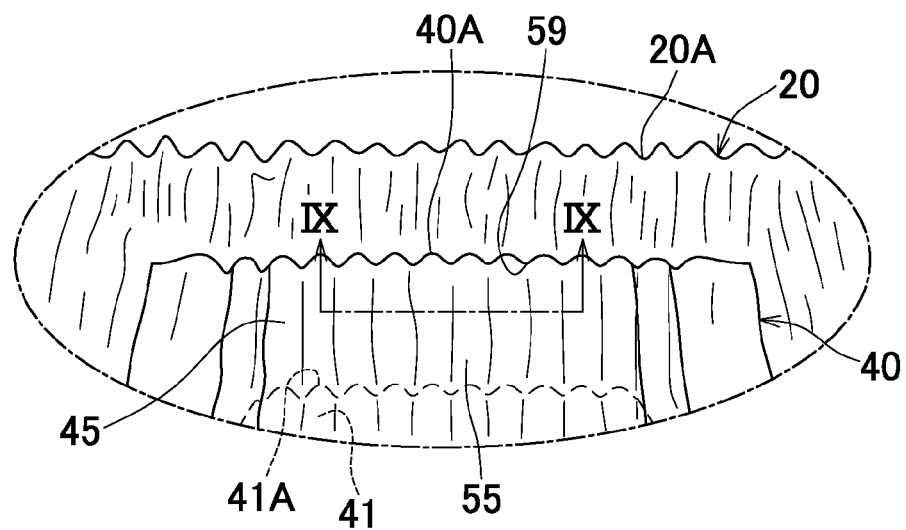

DISPOSABLE WEARING ARTICLE

RELATED APPLICATION

This application is a 35 U.S.C. § 371 national phase filing of International Patent Application No. PCT/JP2013/053465, filed Feb. 14, 2013, through which and to which priority is claimed under 35 U.S.C. § 119 to Japanese Patent Application No. 2012-049752, filed Mar. 6, 2012.

TECHNICAL FIELD

The present invention relates to disposable wearing articles and more particularly to disposable wearing articles such as disposable diapers, disposable toilet-training pants, disposable incontinent pants and disposable sanitary pants each including an elastically contractible waist region.

BACKGROUND

Conventionally, disposable wearing articles are known which include front and rear waist panels defining front and rear waist regions, respectively, and a crotch panel located between these waist panels, the front and rear waist panels are elastically contractible. For example, the Patent Literature 1 discloses a disposable diaper having a front waist panel and a rear waist panel being spaced apart from each other in a longitudinal direction and an absorbent structure adapted to be secured to the front and rear waist panels wherein the front and rear waist panels are provided with a plurality of elastics, respectively, attached thereto under tension in a transverse direction. None of the elastics is present in regions of the front and rear waist panels overlapping with the absorbent structure.

CITATION LIST

Patent Literature

{PTL 1}: JP 2011-115484 A

SUMMARY

Technical Problem

According to the disclosure of PTL 1, none of the elastics is present in the respective regions of both the front waist panel and the rear waist panel adapted to overlap with the absorbent structure. Particularly on the front side of the diaper, the absorbent structure is apt to be partially spaced away from the wearer's skin due to movements of the wearer's body, particularly due to bending and stretching of the wearer's legs. Such portions of the absorbent structure spaced away from the wearer's skin interfere with quick absorption of urine. However, if a tensile stress of the elastics arranged along lateral edges of the absorbent structure is enhanced or the elastics are arranged also in the regions of the both waist sheets adapted to overlap with the absorbent structure to keep the absorbent structure in contact with the wearer's skin, there is a likelihood that the absorbent structure might be kept always in excessively tight contact with the wearer's skin, generating stuffiness within the diaper and eventually causing the wearer's skin to suffer from skin eruption.

An object of the present invention is to provide a wearing article improved so that an absorbent structure is not apt to be spaced away from the wearer's skin but stuffiness and eruption of the wearer's skin can be reliably prevented.

Solution to Problem

The present invention relates to a disposable wearing article having a longitudinal direction and a transverse direction, and including a skin-facing surface, a non-skin-facing surface opposite to the skin-facing surface, front and rear waist panels defining front and rear waist regions, respectively, and elastically contractible in the transverse direction and a crotch panel extending in the longitudinal direction between the front and rear waist panels and defining a crotch region.

The disposable wearing article according to the present invention further includes the following features:

the crotch panel includes an absorbent structure, front and rear end flaps lying outboard of the absorbent structure in the longitudinal direction, a first region including part of the absorbent structure and the front end flap and overlapping with the skin-facing surface of the front waist panel, and a second region including part of the absorbent structure and the rear end flap and overlapping with the skin-facing surface of the rear waist panel;

the first and second regions are joined to the front and rear waist panels by means of first and second joining zones, respectively, wherein the first joining zone has a plurality of sub-zones spaced apart from one another in the transverse direction;

the front waist panel has an elastic region at least overlapping with the first region and elastically contractible in the transverse direction;

the rear waist panel has an inelastic region lying in the second region and overlapping with the absorbent structure and an elastic region lying outboard of the inelastic region as viewed in the transverse direction and elastically contractible in the transverse direction; and the first region is formed with a plurality of convexities extending in the longitudinal direction and spaced apart from one another in the transverse direction.

Advantageous Effects of Invention

According to the present invention, particularly to one or more embodiments thereof, the first region of the front waist panel overlapping with the crotch panel has the elastic region elastically contractible in the transverse direction so that the first region can be kept in close contact with the wearer's body. A plurality of convexities formed in the first region so as to be spaced apart from one another in the transverse direction so that the air conduits may be defined between each pair of the adjacent convexities through which an undesirable stuffiness within the wearing article can be prevented. Between each pair of the adjacent convexities, the skin-facing surface of the wearing article may be kept out of contact with the wearer's skin and, as a result, the wearer can be protected from skin troubles such as skin eruption.

BRIEF DESCRIPTION OF DRAWINGS

FIG. 8 (a) is a scale-enlarged view of a portion encircled by ellipsoidal line VIII in FIG. 2 and FIG. 8 (b) is a schematic diagram corresponding to FIG. 8 (a).

DESCRIPTION OF EMBODIMENTS

Figure 1:
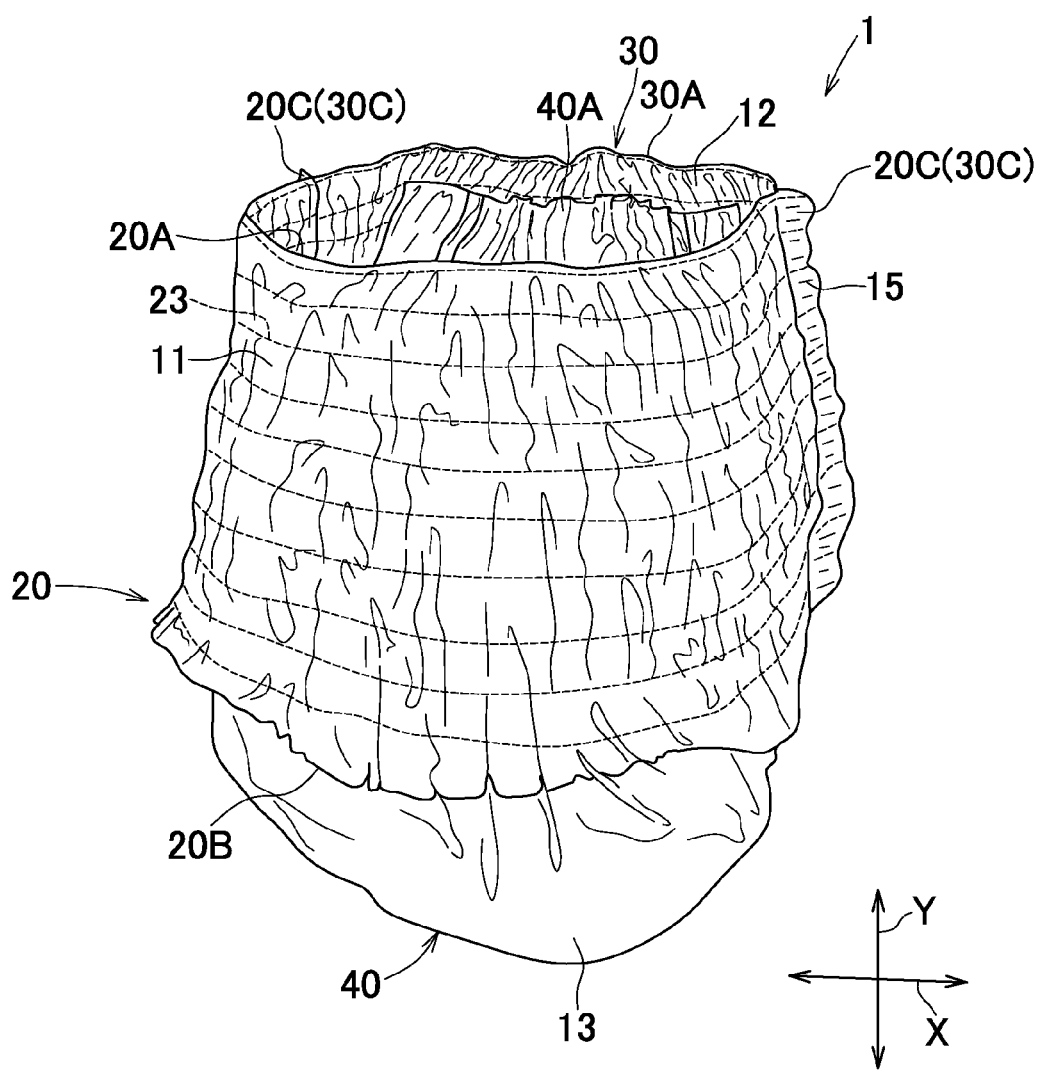
FIG. 1 is a perspective view illustrating a disposable diaper as an example of a disposable wearing article as viewed from the side of a front waist region thereof.
Figure 2:
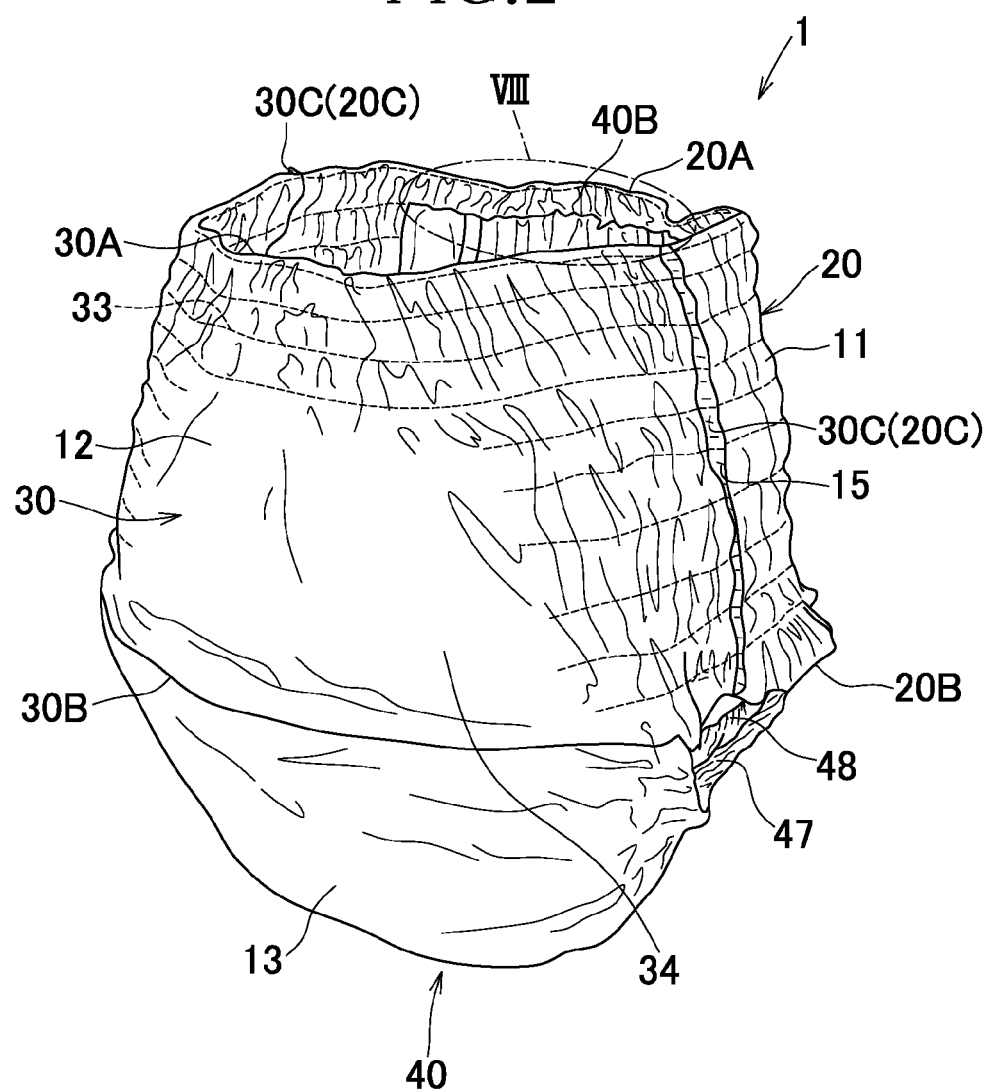
FIG. 2 is a perspective view illustrating the disposable diaper as viewed from the side of a rear waist region thereof.

Referring to FIGS. 1 and 2, a disposable diaper 1 includes a skin-facing side, a non-skin-facing side opposite to the skin-facing side, a front waist region 11, a rear waist region 12 and a crotch region 13 extending between the front and rear waist regions 11, 12. The diaper 1 includes a front waist panel 20 defining the front waist region 11, a rear waist panel 30 defining the rear waist region 12 and a crotch panel 40 defining the crotch region 13 and extending into the front and rear waist regions 11, 12. The front and rear waist panels 20, 30 are joined to each other along a pair of series of seams 15 continually extending in a longitudinal direction Y along respective opposite lateral edges 20C, 30C of the front and rear waist panels 20, 30. The front and rear waist panels 20, 30 respectively have outer ends 20A, 30A extending in a transverse direction X so as to define a waist opening and inner ends 20B, 30B opposed to the outer ends 20A, 30A, respectively, and to define respective parts of leg-openings.

Figure 3:
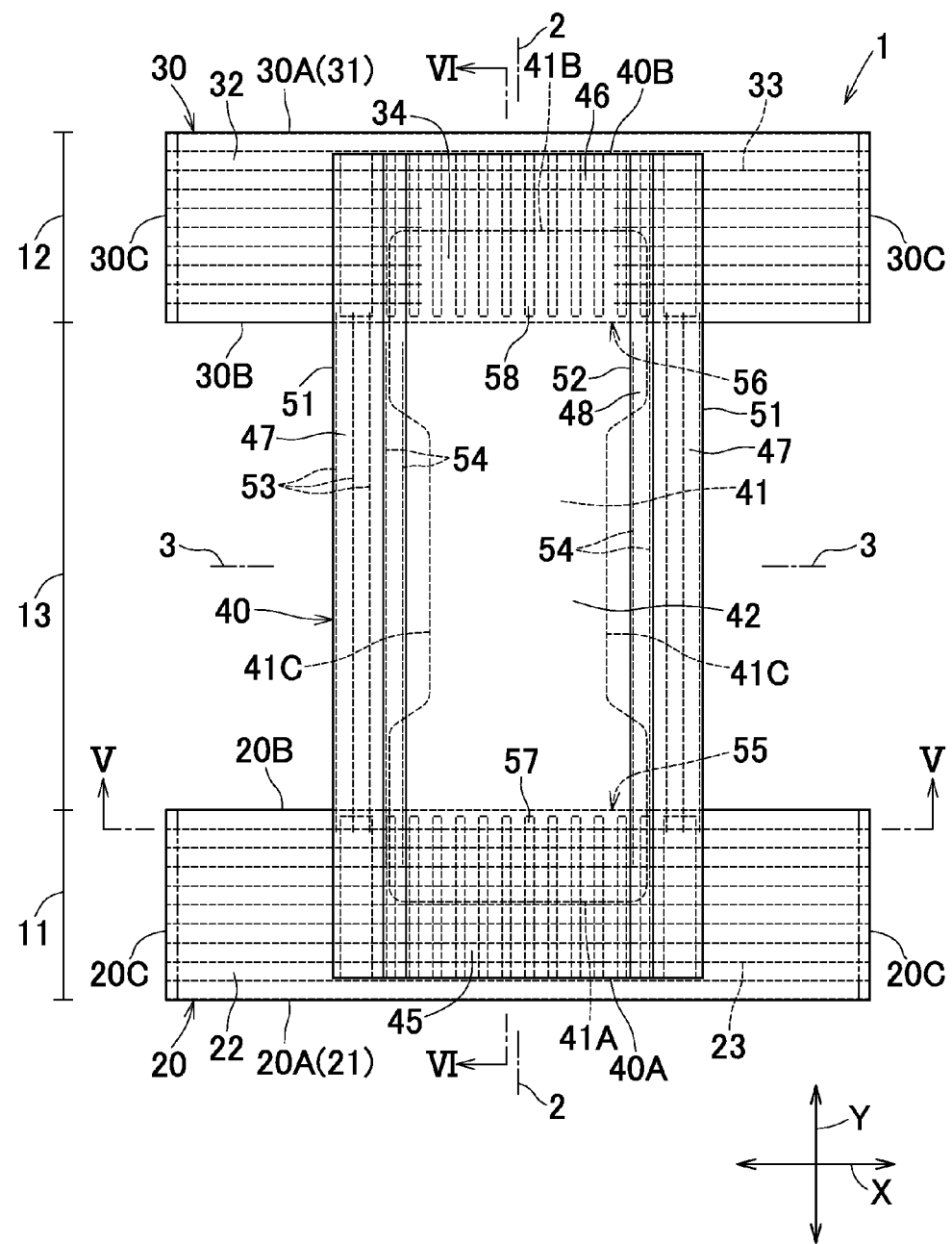
FIG. 3 is a developed plan view illustrating the disposable diaper as viewed from the side of the skin-facing surface thereof.
Figure 4:
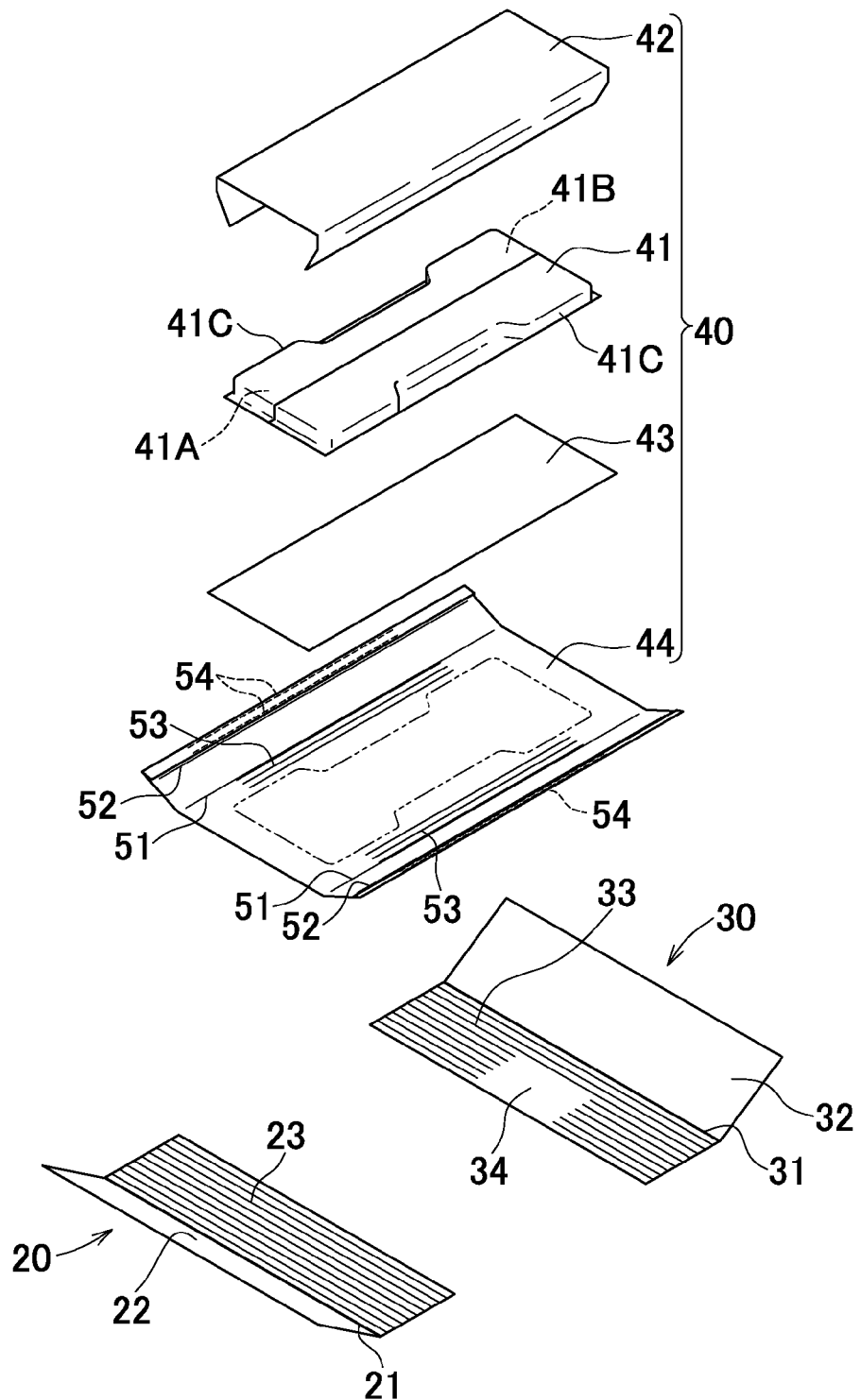
FIG. 4 is an exploded perspective view illustrating the disposable diaper.

Referring now to FIGS. 3 and 4, the diaper 1 has a longitudinal imaginary center line 2-2 bisecting a dimension of the diaper 1 in the transverse direction X and a transverse imaginary center line 3-3 bisecting a dimension of the diaper 1 in the longitudinal direction Y and the diaper 1 is symmetric about the longitudinal imaginary center line 2-2. The front waist panel 20 has a front waist sheet 22 folded along a fold line 21 extending in the transverse direction X onto itself and a plurality of elastics 23 attached between two layers of the front waist sheet 22 having been folded onto itself. The elastics 23 extend in the transverse direction X and are contractibly attached under tension, thereby elasticizing the front waist panel 20 in the transverse direction X. Opposed layers of the front waist sheet 22 having been folded onto itself are joined to each other with the use of well known bonding means such as a hot melt adhesive through the medium of the elastics 23.

The rear waist panel 30 has a rear waist sheet 32 folded along a fold line 31 extending in the transverse direction X onto itself and a plurality of elastics 33 attached between two layers of the rear waist sheet 32 having been folded onto itself. The elastics 33 extend in the transverse direction X and are contractibly attached under tension, thereby elasticizing the rear waist panel 30 in the transverse direction X. Opposed layers of the rear waist sheet 32 having been folded onto itself are joined to each other with the use of known bonding means such as a hot melt adhesive through the medium of the elastics 33.

FIGS. 3 and 4 illustrate the front and rear waist panels 20, 30 in the state stretched in the longitudinal direction Y as well as in the transverse direction X against a contractile force of the elastics 23, 33. In this state, both the front and rear waist sheets 22, 32 have generally rectangular shapes of which dimensions in the transverse direction X are coextensive with one another. As materials of the front and rear waist sheets 22, 32, for example, a spun bonded fibrous nonwoven fabric or a spun bonded/melt blown/spun bonded (SMS) fibrous nonwoven fabric each having a mass per unit area in a range of about 10 to about 40 $g/m^2$, preferably in a range of about 11 to about 20 $g/m^2$ may be used.

The crotch panel 40 includes an absorbent structure 41 containing a liquid-absorbent core material, a body-side liner 42 secured to an absorbing surface of the absorbent structure 41, a leakage-barrier sheet 43 secured to a bottom surface of the absorbent structure 41 and a containment sheet 44 wrapping the body-side liner 42 and the leakage-barrier sheet 43 so as to define an outer side of the crotch panel 40. The body-side liner 42, the leakage-barrier sheet 43 and the containment sheet 44 have respective dimensions in the longitudinal direction Y which are coextensive with one another so as to define front and rear ends 40A, 40B of the crotch panel 40 extending in the transverse direction X. The absorbent structure 41 is dimensioned in the longitudinal direction Y to be smaller than those of the body-side liner 42, the leakage-barrier sheet 43 and the containment sheet 44 so that front and rear end flaps 45, 46 may be formed outboard of the absorbent structure 41 as viewed in the longitudinal direction Y. More specifically, the front and rear end flaps 45, 46 are defined between front and rear end portions 41A, 41B of the absorbent structure 41 extending in the transverse direction X and the front and rear ends 40A, 40B of the crotch panel 40, respectively.

Figure 5:
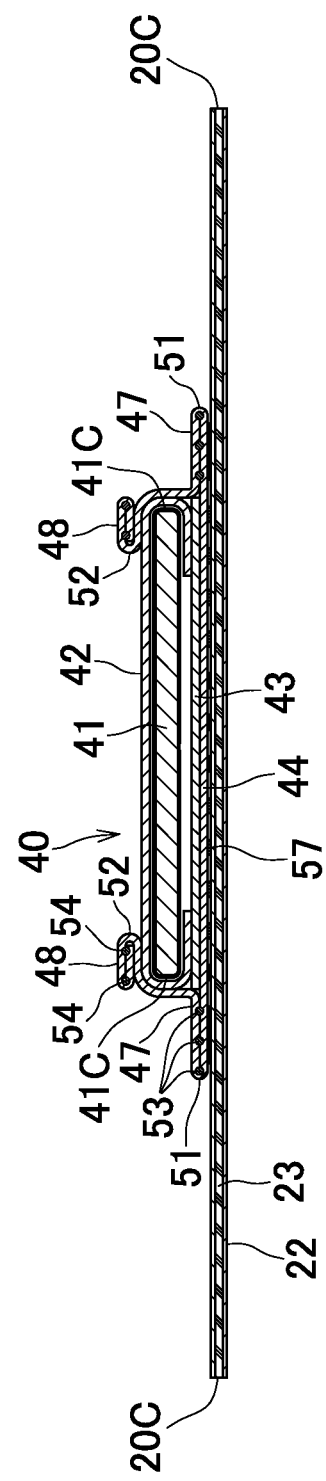
FIG. 5 is a sectional view taken along line V-V in FIG. 3.

Referring to FIG. 5, the containment sheet 44 extends outwardly beyond opposite lateral edges 41C of the absorbent structure 41 and these extensions are folded along first fold lines 51 toward the longitudinal imaginary center line 2-2 to form a pair of side flaps (containment cuffs) 47 which are spaced apart from each other in the transverse direction X. From the state overlapping with the absorbent structure 41, these side flaps 47 are folded along second fold lines 52 extending in the longitudinal direction Y outwardly in the transverse direction X to form a pair of containment flaps 48 spaced apart from each other in the transverse direction X. These flaps 47, 48 are respectively provided with elastics 53, 54 extending in the longitudinal direction Y contractibly attached thereto under tension. The side flaps 47 are adapted to be put in close contact mainly with the wearer's thighs and the containment flaps 48 are adapted, inboard of the side flaps 47, to be put in close contact mainly with the wearer's inner regions. In this manner, the side and containment flaps 47, 48 can prevent body exudates from leaking sideways (See FIG. 2).

As the core material constituting the absorbent structure 41, for example, wood fluff pulp, superabsorbent polymer particles or a mixture thereof may be used. The core material is wrapped with a liquid-permeable and liquid-diffusible sheet such as tissue paper. A mass per unit area of the core material may be in a range of about 320 to about 700 $g/m^2$, preferably in a range of about 320 to about 500 $g/m^2$. As materials of the body-side liner 42, for example, a spun bonded fibrous nonwoven fabric or a point bonded fibrous nonwoven fabric preferably each being hydrophilized and having a mass per unit area in a range of about 15 to about 35 $g/m^2$, preferably in a range of about 18 to about 23 $g/m^2$ may be used. As materials of the leakage-barrier sheet 43, a breathable and liquid-impermeable plastic film or a laminate of this film and a hydrophobic fibrous nonwoven fabric may be used.

As materials of the containment sheet 44, for example, an SMS fibrous nonwoven fabric or a spun bonded fibrous nonwoven fabric each having a mass per unit area in a range of about 10 to about 30 g/m² may be used. As the elastics 53, 54, thread, strand or string elastics having a fineness in a range of about 400 to about 1200 dtex may be used and contractibly attached at an elongation ratio in a range of about 2.0 to about 3.0.

Figure 6:
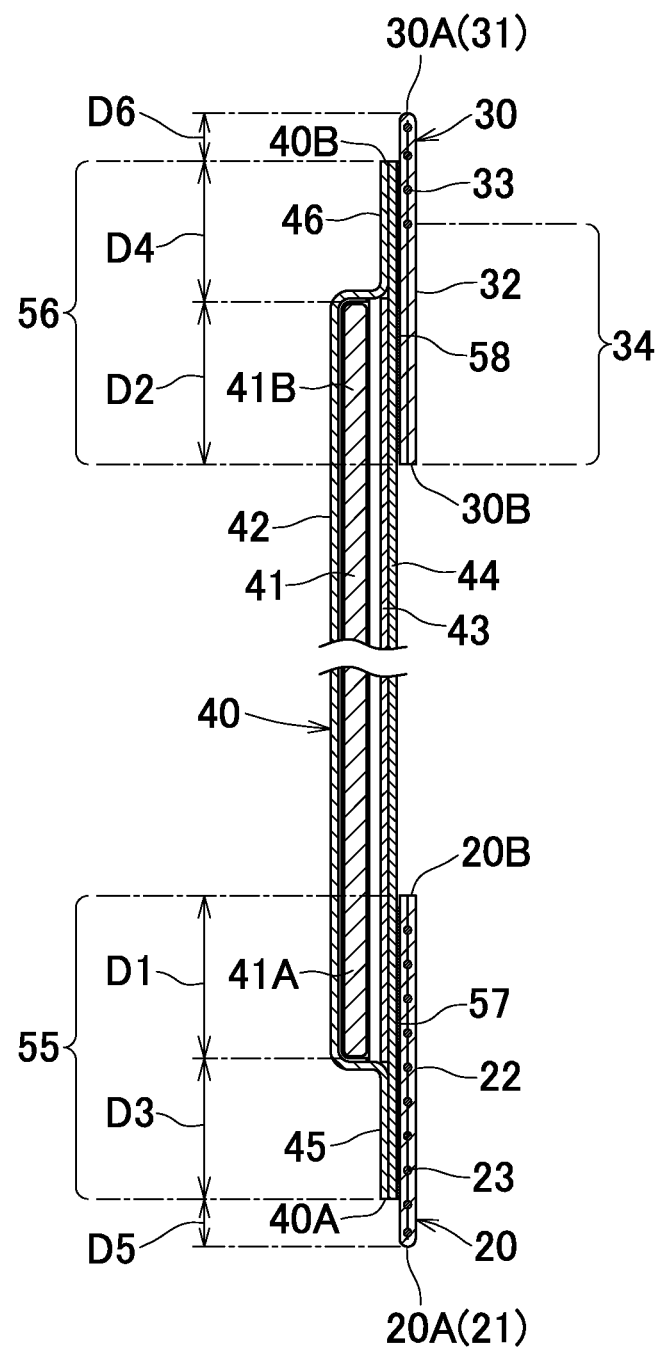
FIG. 6 is a sectional view taken along line VI-VI in FIG. 3.

Now referring to FIG. 6, the crotch panel 40 includes a first region 55 overlapping with the front waist panel 20 and a second region 56 overlapping with the rear waist panel 30. The first region 55 includes the front end portion 41A of the absorbent structure 41 and the front end flap 45 and the second region 56 includes the rear end portion 41B of the absorbent structure 41 and the rear end flap 46. In the first and second regions 55, 56, the first and second regions 55, 56 are joined to the skin-facing side of the front and rear waist panels 20, 30 in first and second joining zones 57, 58, respectively.

In this regard, referring to FIG. 3, the first and second regions 55, 56 include also the side and containment flaps 47, 48. The containment flaps 48 are secured to the body-side liner 42 in a region in which the containment flaps 48 overlap with the absorbent structure 41 (not shown).

Referring again to FIG. 6, dimensions D1 and D2 in the longitudinal direction Y of respective portions of the absorbent structure 41 adapted to overlap the first and second regions 55, 56 are in a range of about 20 to about 120 mm, dimensions D3 and D4 in the longitudinal direction Y of the front and rear end flaps 45, 46 are in a range of about 10 to about 40 mm. Dimensions D5 and D6 in the longitudinal direction Y measured from the front and rear ends 40A, 40B of the crotch panel 40 to the outer ends 20A, 30A of the front and rear waist panel 20, 30 are in a range of about 5 to about 100 mm.

Figure 7:
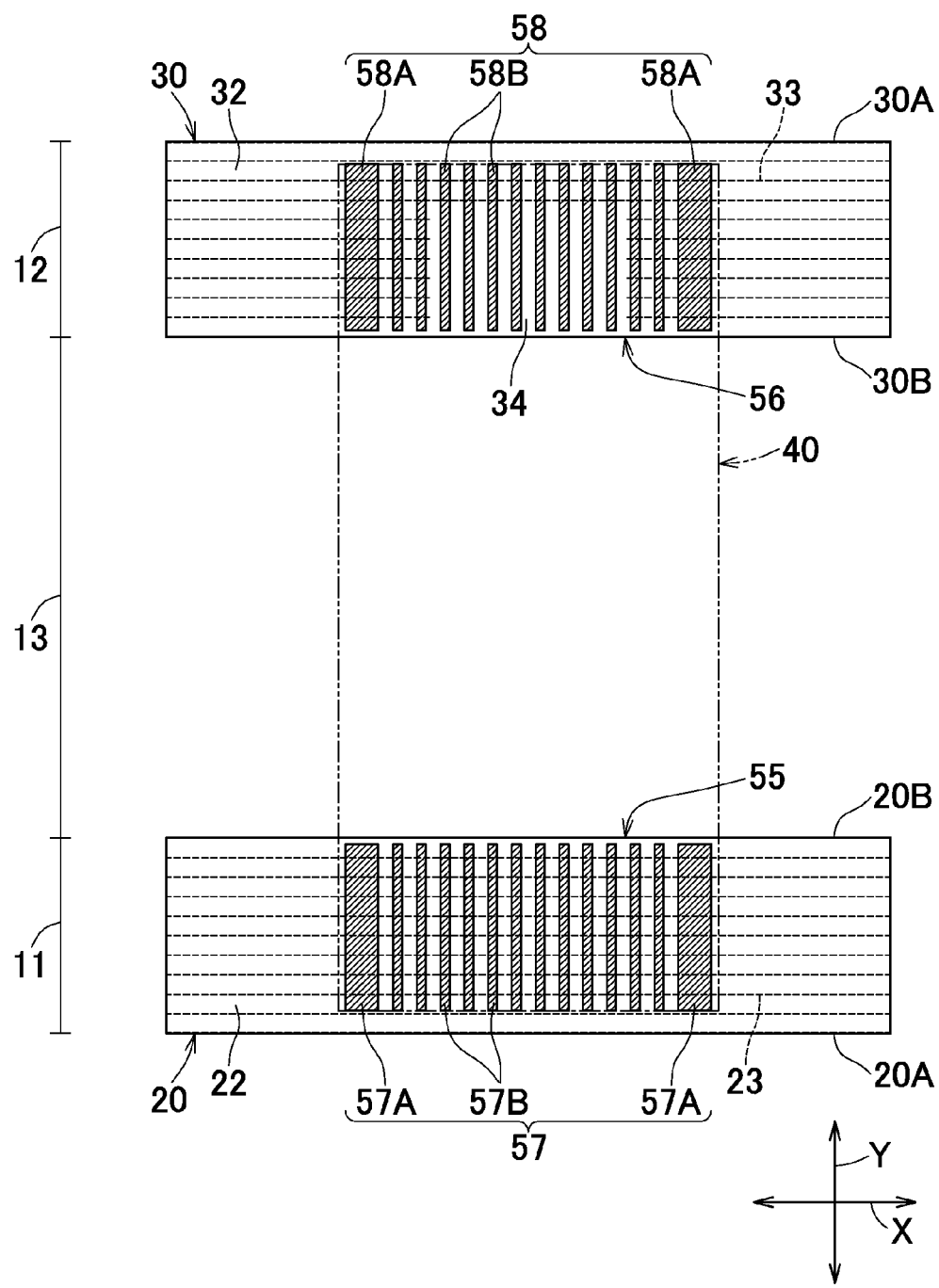
FIG. 7 is a view similar to FIG. 3 except that the crotch panel is not illustrated.

Referring to FIG. 7, the first and second joining zones 57, 58 extend in the longitudinal direction Y in the first and second regions 55, 56, respectively, each including a plurality of zones arranged to be spaced apart from each other in the transverse direction X. The first and second joining zones 57, 58 respectively include a pair of the outermost sub-zones 57A, 58A and intermediate sub-zones 57B, 58B arranged inboard of the respective pairs of the outermost sub-zones in the transverse direction X. Each of the outermost sub-zones 57A, 58A has a dimension in the transverse direction X in a range of about 2 to about 20 mm, and about 10 mm in the illustrated embodiment. Each of the intermediate joining sub-zones 57B, 58B has a dimension in the transverse direction X in a range of about 2 to about 20 mm and about 5 mm in the illustrated embodiment. In other words, each dimension of the intermediate joining sub-zones 57B, 58B in the transverse dimension is smaller than each dimension of the outermost joining sub-zones 57A, 58A in the transverse direction. The first and second joining zones 57, 58 are respectively arranged so as to be spaced apart from each other by about 1 to about 10 mm and about 6 mm in the illustrated embodiment. The first and second joining zones 57, 58 may be formed, for example, of well known bonding means such as a hot melt adhesive.

The front waist panel 20 is provided over its entire area with the elastics 23 to define an elastic region adapted to be elastically contractible in the transverse direction X. As a material of the elastics 23, a plurality of thread, string or strand elastics each having a fineness, for example, in a range of about 400 to about 1200 dtex may be used and these elastics may be arranged at pitches in a range of about 4 to about 12 mm in the longitudinal direction Y at an elongation ratio in a range of about 1.7 to about 3.5. In the illustrated embodiment, four elastics each having a fineness of 470 dtex are arranged at an elongation ratio of about 2.4, four elastics each having a fineness of 940 dtex are arranged at an elongation ratio of about 2.1 and two elastics having a fineness of 470 dtex are arranged at an elongation ratio of about 2.1 from the outer end 20A toward the inner end 20B of the front waist panel 20.

A region of the rear waist panel 30 overlapping with the absorbent structure 41 defines an inelastic region 34 in which none of the elastics 33 is present. The inelastic region 34 may be defined by arranging none of the elastics 33 in this region or, after the elastics 33 have been arranged in this region 34, by cutting and snapping back these elastics 33 so that substantially no elasticity may be exerted on this region. Outboard of the inelastic region 34 in the transverse direction X as well as in the longitudinal direction Y, an elastic region subjected to the elasticity of the elastics 33 is formed. This elastic region is defined so as to surround the inelastic region 34 with a pair of square U-shape sub-regions. As a material of the elastics to be arranged in this elastic region, a plurality of thread, string or strand elastics, for example, each having a fineness in a range of about 400 to about 1200 dtex may be attached at pitches in the longitudinal direction Y in a range of about 4 to about 12 mm under tension at an elongation ratio in a range of about 1.7 to about 3.5. According to the illustrated embodiment, outboard of the inelastic region 34 in the longitudinal direction Y, four elastics each having a fineness of 940 dtex are attached at an elongation ratio of about 2.4 and, outboard of the inelastic region 34 in the transverse direction X, one elastic having a fineness of 940 dtex is attached at an elongation ratio of about 2.1, three elastics each having a fineness of 940 dtex are attached at an elongation ratio of about 3.0 and two elastics each having a fineness of 470 dtex are contractibly attached at an elongation of about 3.0.

Figure 9:
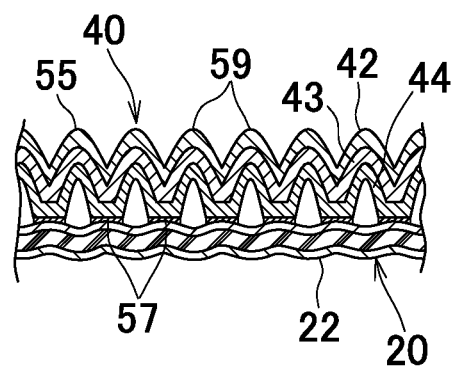
FIG. 9 is a sectional view taken along line IX-IX in FIG. 8 (b).

In the diaper 1 as has been described above, the front and rear waist panels 20, 30 contract in the transverse direction X under the effect of the elastics 23, 33. As illustrated in FIGS. 8 and 9, the first region 55 of the crotch panel 40 is formed on the skin-facing side with convexities 59 in response to contraction of the front waist panel 20. Specifically, the first region 55 contracts in response to contraction of the front waist panel 20 in the transverse direction X and, in consequence, this first region 55 is formed with gathers extending in the longitudinal direction Y. the first joining zone 57 overlapping with the first region 55 are apt to be wrinkled and these wrinkles form a plurality of the convexities. Particularly between each pair of the adjacent first joining zones 57, the crotch panel 40 is not joined to the front waist panel 20 and therefore the crotch panel 40 is apt to be spaced apart from the front waist panel 20 so as to form the convexities.

In the first region 55, the front end flap 45 has its stiffness lower than that of the portion overlapped by the absorbent structure 41 and is correspondingly easy to be gathered and to form the convexities 59. As for the absorbent structure 41, a mass per unit area of the core material is as low as about 320 to about 700 g/m² and, in consequence, even the portion thereof overlapping with the absorbent structure 41 is formed with a plurality of the convexities 59 extending in the longitudinal direction Y as if in response to the convexities formed particularly in the front end flap 45. To facilitate the absorbent structure 41 also to be formed with the convexities 59, a mass per unit area of the absorbent structure 41 is preferably as further low as about 320 to about 500 g/m², but if the mass per unit area thereof is lower than 320 g/m², there is a likelihood that the absorbent structure 41 might not completely absorb urine and eventually urine might leak out of the diaper 1. The convexities 59 formed in the manner as has been described above allows an area of the absorbent structure 41 put in direct contact with the wearer's skin to be reduced and whereby skin eruption due to direct contact of the wearer's skin with the absorbent structure can be prevented.

The convexities 59 formed in the first region 55 extend along the first joining zones 57 in the longitudinal direction Y, thereby defining air conduits extending from the crotch region 12 to vicinities of the outer end 20A of the front waist panel 20. A dimension from the front end 40A of the crotch panel 40 to the outer end 20A of the front waist panel 20 is extremely small and, as a result, air within the diaper 1 easily move outwardly through the air conduits defined by the convexities 59, thereby preventing a stuffiness in the diaper 1.

In the rear waist panel 30, the inelastic region 34 is free from influence of the contractile force of the elastics 33 and, in consequence, substantially no wrinkle may be formed in this region (See FIG. 2). Consequently, in the inelastic region 34, the absorbent structure 41 can be put in close contact, over an area as large as possible, with the wearer's skin and can quickly absorb bodily exudates. During the use of the diaper 1, the wearer's excretory organ is located to face a zone of the crotch region 13 nearer to the rear waist region 12 and bodily exudates are apt to move toward the rear waist region 12. However, in the second region 56 lying in the rear waist region 12, the segment of the absorbent structure 41 lying in the inelastic region 34 is put in close contact with the wearer's body to absorb bodily exudates quickly and whereby the leakage of bodily exudates beyond the outer end 30A of the rear waist panel 30 can be prevented. Particularly for the wearer lying in a bed most of a day, such as a newborn baby, bodily exudates would otherwise be apt to leak out beyond the outer end of the rear waist region 12. However, the segment of the absorbent structure 41 in the second region 56 may be put in close contact with the wearer's body to prevent such possibility.

When the inelastic region 34 is arranged to overlap the absorbent structure 41 as has been described above, the absorbent structure 41 might be likely to be spaced away from the wearer's body due to the movement of the wearer's body. Considering this, the elastics 33 attached to the rear waist panel 30 are arranged in the illustrated embodiment so that the elastics 33 may partially overlap the opposite lateral edges 41C of the absorbent structure 41 (See FIG. 3). In this way, the opposite lateral edges 41C of the absorbent structure 41 are put in tight contact with the wearer's body under the contractile force of the elastics 33 and thus it is possible to prevent the entirety of the absorbent structure 41 from being spaced away from the wearer's body.

Outboard of the inelastic region 34 in the longitudinal direction Y, the rear end flap 46 is provided with the elastics 33 so as to be formed with an elastic region and, in addition, provided with a second joining zone 58. With such an arrangement, this rear end flap 46 is formed with gathers extending in the longitudinal direction along the second joining zones 58 and there is a possibility that the inelastic region 34 also might be formed with gathers conforming to the gathers formed in the rear end flap 46. However, if these gathers are formed in the inelastic region 34, the number thereof will be much fewer than the convexities 59 formed on the absorbent structure 41 in the first region 55 and the size thereof also will be much smaller than those in the first region 55. Thus, the wrinkles formed in the second region 56 are permissible so long as these wrinkles do not affect the desired close contact of the second region 56 with the wearer's body.

The front waist panel 20 is contracted near over its entire area in the transverse direction X and a dimension in the transverse direction X of the segment of the front waist panel 30 overlapping with the absorbent structure 41 becomes smaller than that of the rear waist panel 30. In response to contraction of the front waist panel 20 in the transverse direction X, the first region 55 of the crotch panel 40 is contracted, i.e., the entire front region of the crotch region 13 is contracted in the transverse direction X. As a result, the crotch panel should not clog movements of the wearer's legs.

At least the portion of the rear waist panel 30 overlapping with the absorbent structure 41 is not contracted at all and therefore the second regions 56 is free from a noticeable contraction. Assuming that the second region 56 is noticeably contracted, the region adapted to cover the wearer's buttocks will be constricted and eventually expose the buttocks and/or cause bodily exudates to leak out. However, with the arrangement according to the illustrated embodiment, such problems can be prevented.

As has been described above, the dimension of the diaper in the transverse direction X on the side of the front waist panel 20 may become relatively small while the dimension of the diaper in the transverse direction X on the side of the rear waist panel 30 may become relatively large under contraction of the elastics 23, 33, whereby, in the state of the diaper flatly developed against the contractile force of these elastics 23, 33, the front and rear waist sheets 22, 32 adapted to define the front and rear waist panels 20, 30 may be configured to have the same dimension and, in addition, the crotch panel 40 may be configured to have the same dimension in the front and rear portions thereof in the transverse direction. In other words, the respective lateral edges of the front and rear waist panels 20, 30 and the crotch panel 40 may be contoured by straight lines substantially extending in parallel to the longitudinal imaginary center line 2-2. With such an arrangement, the diaper can be more easily manufactured than where the step of trimming along complicated contouring line and, as a result, a trimming loss also can be reduced.

Regarding the first and second joining zones 57, 58, the dimension in the transverse direction X of the respective outermost sub-zones 57A, 58A are larger than those of the intermediate sub-zones 57B, 58B. By dimensioning the outermost sub-zones 57A, 58A larger than the intermediate sub-zones 57B, 58B, the crotch panel 40 can be joined to the front and rear waist panels 20, 30 more reliably in the outermost sub-zones 57A, 58A than in the intermediate sub-zones 57B, 58B and whereby it is possible to prevent the crotch panel 40 from being peeled off from the front and rear waist panels 20, 30 beginning at the outermost sub-zones 57A, 58A. In this regard, the present invention is not limited to such an arrangement but it is also possible to configure the dimensions of the outermost sub-zones and the intermediate sub-zones to be the same and also to configure each dimension of the intermediate sub-zones to be larger than that of the outermost sub-zones.

The front and rear waist panels 20, 30 respectively have elastically contractible regions between the first and second joining zones 57, 58 and the outer ends 20A, 30A as viewed in the longitudinal direction Y. These outer ends 20A, 30A cooperate with each other to form the waist-opening and therefore the diaper 1 is put in close contact with the wearer's body at least along the periphery of the waist-opening to prevent bodily exudates from leaking out of the diaper.

The disclosure relating to the present invention as has been described hereinabove may be rearranged as follows:

The disposable wearing article 1 has the longitudinal direction Y and the transverse direction X and includes the skin-facing surface, the non-skin-facing surface opposite to the skin-facing surface, the front and rear waist panels 20, 30 defining the front and rear waist regions 11, 12, respectively, and elastically contractible in the transverse direction X and the crotch panel 40 extending in the longitudinal direction Y between the front and rear waist panels 20, 30 and defining the crotch region 13.

The disposable wearing article 1 according to the present invention further includes the following features:

the crotch panel 40 includes the absorbent structure 41, the front and rear end flaps 45, 46 lying outboard of the absorbent structure 41 in the longitudinal direction Y, the first region 55 having part of the absorbent structure 41 and the front end flap 45 and overlapping with the skin-facing surface of the front waist panel 20 and the second region 56 having part of the absorbent structure and the rear end flap 46 and overlapping with the skin-facing surface of the rear waist panel 30;

the first and second regions 55, 56 are joined to the front and rear waist panels 20, 30 by means of the first and second joining zones 57, 58, respectively, wherein the first joining zone 57 has a plurality of sub-zones spaced apart from one another in the transverse direction X;

the front waist panel 20 has the elastic region at least overlapping with the first region 55 and being elastically contractible in the transverse direction X and the rear waist panel 30 has the inelastic region 34 lying in the second region 56 and overlapping with the absorbent structure 41 and the elastic region lying outboard of the inelastic region 34 as viewed in the transverse direction X and elastically contractible in the transverse direction X; and the first region 55 is formed with a plurality of the convexities 90 extending in the longitudinal direction Y and spaced apart from one another in the transverse direction X.

The above-mentioned invention may include at least the following embodiments.

(1) With the front and rear waist panels 20, 30 in a contracted state, the portion of the front waist panel 20 overlapping with the absorbent structure 41 has the dimension in the transverse direction X smaller than that of the rear waist panel 30.

(2) The first joining zone 57 extends in the longitudinal direction Y.

(3) The front and rear waist panels 20, 30 respectively have the outer ends 20A, 30A extending in the transverse direction X and cooperating with each other to form the waist-opening and respectively have the elastic regions defined between the first and second joining zones 57, 58 and the outer ends 20A, 30A to be elastically contractible in the transverse direction X.

(4) The crotch panel 40 has the front and rear ends 40A, 40B both extending in the transverse direction X wherein the dimension from the front end 40A to the outer end 20A of the front waist panel 20 as well as the dimension from the rear end 40B to the outer end 30A of the rear waist panel 30 is in a range of 5 to 100 mm.

(5) The elastic regions respectively include the waist sheets 22, 32 and a plurality of the elastics 23, 33 contractibly attached under tension to the respective waist sheets 22, 32 so as to extend in the transverse direction X and to be spaced apart from one another in the longitudinal direction Y.

(6) The respective sub-zones of the first joining zone 57 have a dimension in the transverse direction X in a range of 2 to 20 mm and the distance dimension between each pair of the adjacent joining zones is in a range of 1 to 10 mm.

(7) Of the first joining zone 57, the outermost sub-zones 57A as viewed in the transverse direction X respectively have a dimension in the transverse direction X larger than that of the respective intermediate sub-zones 57B.

(8) The absorbent structure 41 includes the liquid-absorbent core material and the wrapping sheet adapted to wrap the core material wherein a mass per unit area of the core material is in a range of 320 to 700 g/m$^2$.

(9) The crotch panel 40 further includes the body-side liner 42 lying on the absorbing surface of the absorbent structure 41, the leakage-barrier sheet 43 placed on the bottom surface of the absorbent structure 41 and the containment sheet 44 adapted to cover the leakage-barrier sheet 43 and to form the containment cuffs outboard of the absorbent structure 41 as viewed in the transverse direction X wherein the front and rear end flaps 45, 46 are defined by the body-side liner 42, the leakage-barrier sheet 43 and the containment sheet 44.

(10) The front and rear waist panels 20, 30 respectively have the rectangular shapes in the state stretched against the contractile force of the elastics 23, 33 and the dimension in the transverse direction X of the front waist panel 20 is the same as that of the rear waist panel 30.

The constituent elements of the diaper 1 are not limited to those described in the present specification but the other various types of material widely used in the relevant technical field may be used without limitation.

The terms "first" and "second" used in the specification and Claims of the present invention are used merely to distinguish the similar elements, similar position or other similar means.

REFERENCE SIGNS LIST 1 disposable diaper (disposable wearing article)
11 front waist region
12 rear waist region
13 crotch region
20 front waist panel
20A outer end
20B inner end
23 elastics
30 rear waist panel
30A outer end
30B inner end
33 elastics
40 crotch panel
40A front end
40B rear end
41 absorbent structure
41A front end
41B rear end
42 body-side liner
43 leakage-barrier sheet
44 containment sheet
45 front end flap
46 rear end flap
55 first region
56 second region
57 first joining zones 58 second joining zones

The invention claimed is:

1. A disposable wearing article having a longitudinal direction and a transverse direction, including: a skin-facing surface;
   a non-skin-facing surface opposite to the skin-facing surface;
   front and rear waist panels defining front and rear waist regions, respectively, and elastically contractible in the transverse direction; and
   a crotch panel extending in the longitudinal direction between the front and rear waist panels and defining a crotch region, wherein:
   the crotch panel includes an absorbent structure, front and rear end flaps lying outboard of the absorbent structure in the longitudinal direction, a first region having part of the absorbent structure and the front end flap and overlapping with the skin-facing surface of the front waist panel and a second region having part of the absorbent structure and the rear end flap and overlapping with the skin-facing surface of the rear waist panel;
   the first and second regions are joined to the front and rear waist panels by means of first and second joining zones, respectively, wherein the first joining zone has a plurality of sub-zones spaced apart from one another in the transverse direction, which plurality of sub-zones to not do extend outwardly beyond transverse edges of the crotch panel;
   the front waist panel has an elastic region at least overlapping with the first region and elastically contractible in the transverse direction;
   the rear waist panel has an inelastic region lying in the second region and overlapping with the absorbent structure and an elastic region lying outboard of the inelastic region as viewed in the transverse direction and elastically contractible in the transverse direction; and
   the first region is formed with a plurality of convexities extending in the longitudinal direction and spaced apart from one another in the transverse direction.

2. The disposable wearing article according to claim 1, wherein, when the front and rear waist panels are in a contracted state, a portion of the front waist panel overlapping with the absorbent structure has a dimension in the transverse direction smaller than that of the rear waist panel.

3. The disposable wearing article according to claim 2, wherein the first joining zone extends in the longitudinal direction.

4. The disposable wearing article according to claim 2, wherein the front and rear waist panels respectively have the outer ends extending in the transverse direction and cooperating with each other to form a waist-opening and respectively have an elastic regions defined between the first and second joining zones and the outer ends so as to be elastically contractible in the transverse direction.

5. The disposable wearing article according to claim 2, wherein:
   the crotch panel has the front and rear ends both extending in the transverse direction X; and
   a dimension from the front end to the outer end of the front waist panel as well as a dimension from the rear end to the outer end of the rear waist panel is in a range of 5 to 100 mm.

6. The disposable wearing article according to claim 2, wherein the elastic regions respectively include the waist sheets and a plurality of elastics contractibly attached under tension to the respective waist sheets so as to extend in the transverse direction and to be spaced apart from one another in the longitudinal direction.

7. The disposable wearing article according to claim 1, wherein the first joining zone extends in the longitudinal direction.

8. The disposable wearing article according to claim 7, wherein the front and rear waist panels respectively have the outer ends extending in the transverse direction and cooperating with each other to form a waist-opening and respectively have an elastic regions defined between the first and second joining zones and the outer ends so as to be elastically contractible in the transverse direction.

9. The disposable wearing article according to claim 7, wherein:
   the crotch panel has the front and rear ends both extending in the transverse direction X; and
   a dimension from the front end to the outer end of the front waist panel as well as a dimension from the rear end to the outer end of the rear waist panel is in a range of 5 to 100 mm.

10. The disposable wearing article according to claim 7, wherein the elastic regions respectively include the waist sheets and a plurality of elastics contractibly attached under tension to the respective waist sheets so as to extend in the transverse direction and to be spaced apart from one another in the longitudinal direction.

11. The disposable wearing article according to claim 1, wherein the front and rear waist panels respectively have the outer ends extending in the transverse direction and cooperating with each other to form a waist-opening and respectively have an elastic regions defined between the first and second joining zones and the outer ends so as to be elastically contractible in the transverse direction.

12. The disposable wearing article according to claim 11, wherein:
   the crotch panel has the front and rear ends both extending in the transverse direction X; and
   a dimension from the front end to the outer end of the front waist panel as well as a dimension from the rear end to the outer end of the rear waist panel is in a range of 5 to 100 mm.

13. The disposable wearing article according to claim 11, wherein the elastic regions respectively include the waist sheets and a plurality of elastics contractibly attached under tension to the respective waist sheets so as to extend in the transverse direction and to be spaced apart from one another in the longitudinal direction.

14. The disposable wearing article according to claim 1, wherein:
   the crotch panel has the front and rear ends both extending in the transverse direction X; and
   a dimension from the front end to the outer end of the front waist panel as well as a dimension from the rear end to the outer end of the rear waist panel is in a range of 5 to 100 mm.

15. The disposable wearing article according to claim 1, wherein the elastic regions respectively include the waist sheets and a plurality of elastics contractibly attached under tension to the respective waist sheets so as to extend in the transverse direction and to be spaced apart from one another in the longitudinal direction.

16. The disposable wearing article according to claim 1, wherein the respective sub-zones of the first joining zone have a dimension in the transverse direction in a range of 2 to 20 mm and a distance dimension between each pair of the adjacent joining zones is in a range of 1 to 10 mm.

17. The disposable wearing article according to claim 1, wherein, of the first joining zone, outermost sub-zones as viewed in the transverse direction respectively have a dimension in the transverse direction larger than that of respective intermediate sub-zones.

18. The disposable wearing article according to claim 1, wherein the absorbent structure includes liquid-absorbent core material and a wrapping sheet adapted to wrap the core material wherein a mass per unit area of the core material is in a range of 320 to 700 $g/m^2$.

19. The disposable wearing article according to claim 1, wherein the crotch panel further includes a body-side liner lying on an absorbing surface of the absorbent structure, a leakage-barrier sheet placed on a bottom surface of the absorbent structure and a containment sheet adapted to cover the leakage-barrier sheet and to form containment cuffs outboard of the absorbent structure as viewed in the transverse direction, wherein the front and rear end flaps are defined by the body-side liner, the leakage-barrier sheet and the containment sheet.

20. The disposable wearing article according to claim 1, wherein the front and rear waist panels respectively have a rectangular shapes in the state stretched against a contractile force of the elastics and a dimension in the transverse direction of the front waist panel is the same as that of the rear waist panel.

\* \* \* \* \*